US00PP20996P2

(12) United States Plant Patent
Warren

(10) Patent No.: US PP20,996 P2
(45) Date of Patent: May 18, 2010

(54) **JAPANESE *ZELKOVA* TREE NAMED 'JFS-KW1'**

(50) Latin Name: *Zelkova serrata*
Varietal Denomination: JFS-KW1

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 12/288,997

(22) Filed: Oct. 23, 2008

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

| | | | |
|---|---|---|---|
| PP2,337 | P | 1/1964 | Flemer |
| PP5,080 | P | 8/1983 | Flemer |
| PP5,687 | P | 3/1986 | Halka |
| PP17,220 | P3 | 11/2006 | Moon |

OTHER PUBLICATIONS

Recommended Urban Trees: Site Assessment and Tree Selection for Stress Tolerance, Urban Horticulture Institute Department of Horticulture Cornell University, 2009, i-iii and p. 45.*

* cited by examiner

*Primary Examiner*—June Hwu
(74) *Attorney, Agent, or Firm*—Klarquist Sparkman, LLP

(57) ABSTRACT

A variety of Japanese *Zelkova* which combines unusually small leaves, short internodes, slow growth, and dense branching with a compact growth habit and semi-dwarf size.

7 Drawing Sheets

Latin name of the genus and species: *Zelkova serrata.*

Variety denomination: 'JFS-KW1'.

BACKGROUND

During the summer of 2001, I searched through thousands of *Zelkova serrata* seedlings growing in nursery rows in Canby, Oreg. I examined these trees looking for significant seedling variation that might allow for the selection of improved cultivars. During this search, I found one tree which was significantly different from all other seedlings in the field due to its compact, semi-dwarf growth habit and short internode length. I marked and labeled this tree, and directed it to be dug during winter dormancy.

In February, 2002, this original 'JFS-KW1' tree was transplanted into a special row with other trees which were under evaluation at nursery grounds in Boring, Oreg. In September of 2002, I began test propagation of this original 'JFS-KW1' tree by directing the budding onto *Zelkova serrata* rootstock in a nursery in Canby, Oreg. On examining the resulting propagated trees during the summer of 2003, I determined that the tree was fixed in its dwarf characteristics and that it possessed a unique and valuable form. I designated this tree with the cultivar name 'JFS-KW1'.

In 2003 and 2004, I again directed asexual propagation of my new cultivar in small test plots by budding onto *Zelkova serrata* rootstock at a nursery in Canby, Oreg. I then evaluated the growth characteristics of trees in each plot during the following three years. In February of 2007, I also asexually propagated a small test plot of trees of my new cultivar by top grafting at a two meter height onto *Zelkova serrata* seedling trunks growing at a nursery in Canby, Oreg. I evaluated these trees during the next two growing seasons. This asexual propagation has shown that the unique characteristics of my new tree are firmly fixed in each successive generation.

SUMMARY

This new cultivar possesses a unique combination of characteristics in that it combines unusually small leaves, short internodes, and dense branching with a compact growth habit and semi-dwarf size.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
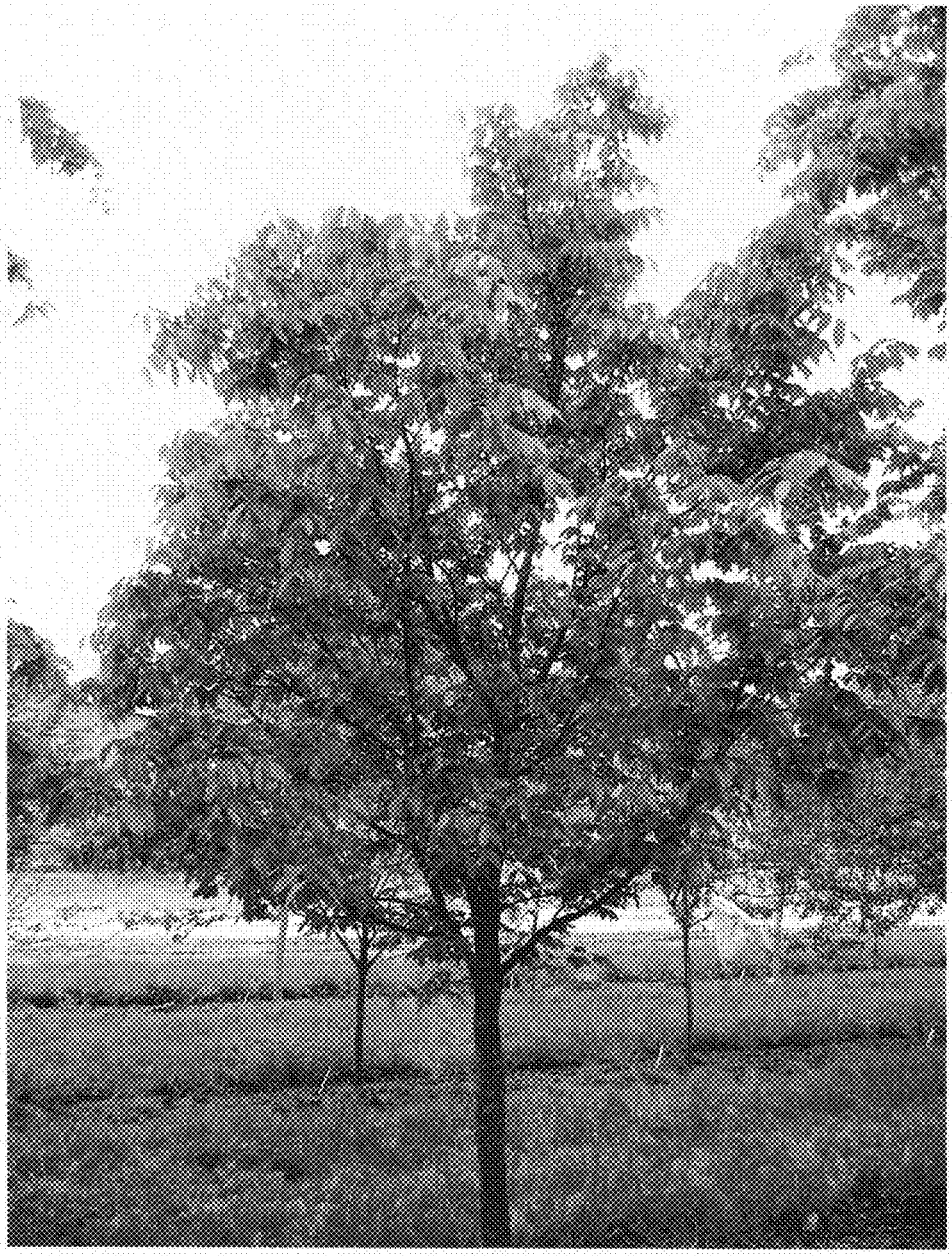
FIG. 1: Shows the original tree at 10 years of age in spring foliage.
Figure 2:
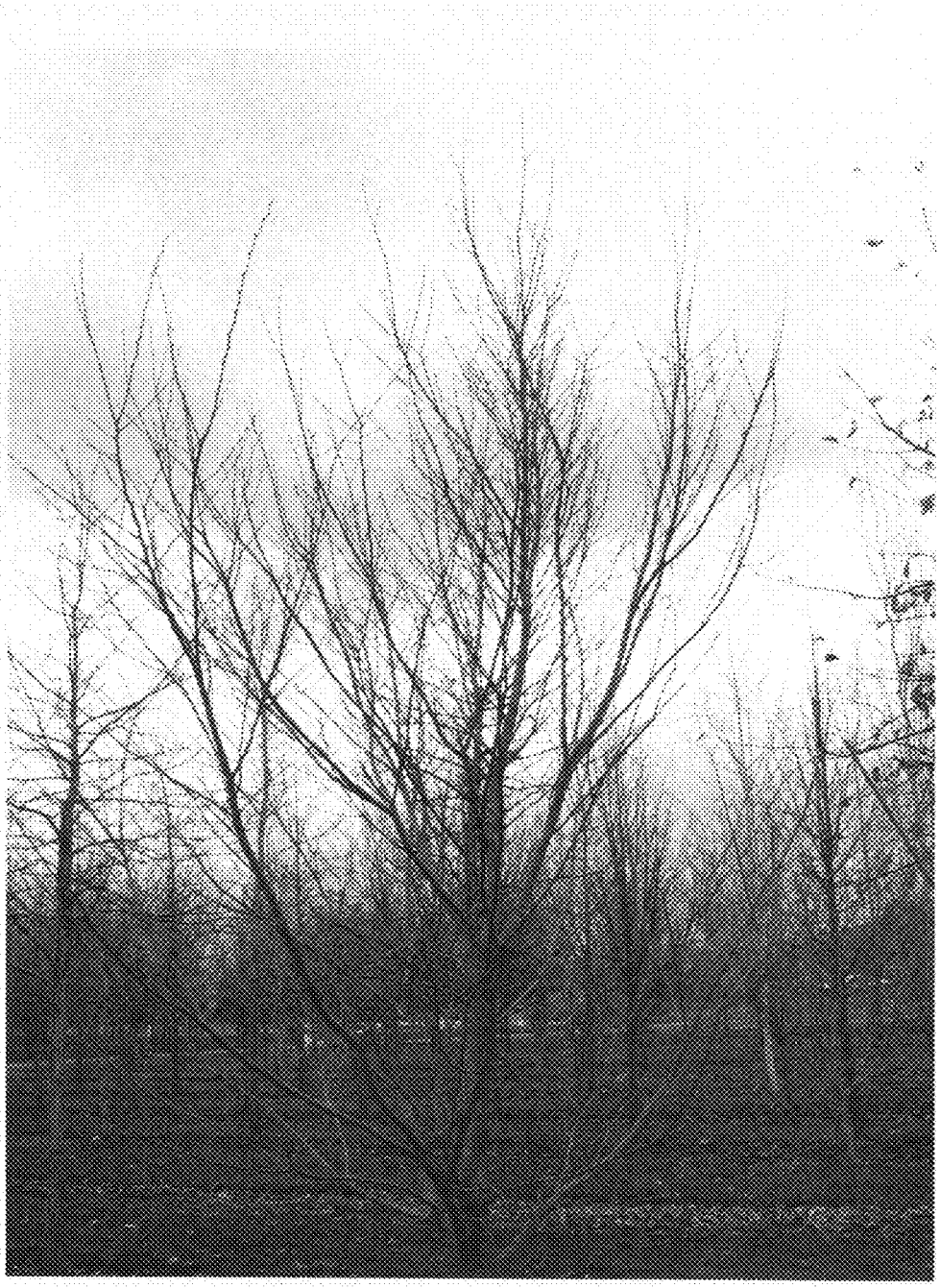
FIG. 2: Shows a portion of the original tree during dormancy at 9 years of age.
Figure 3:
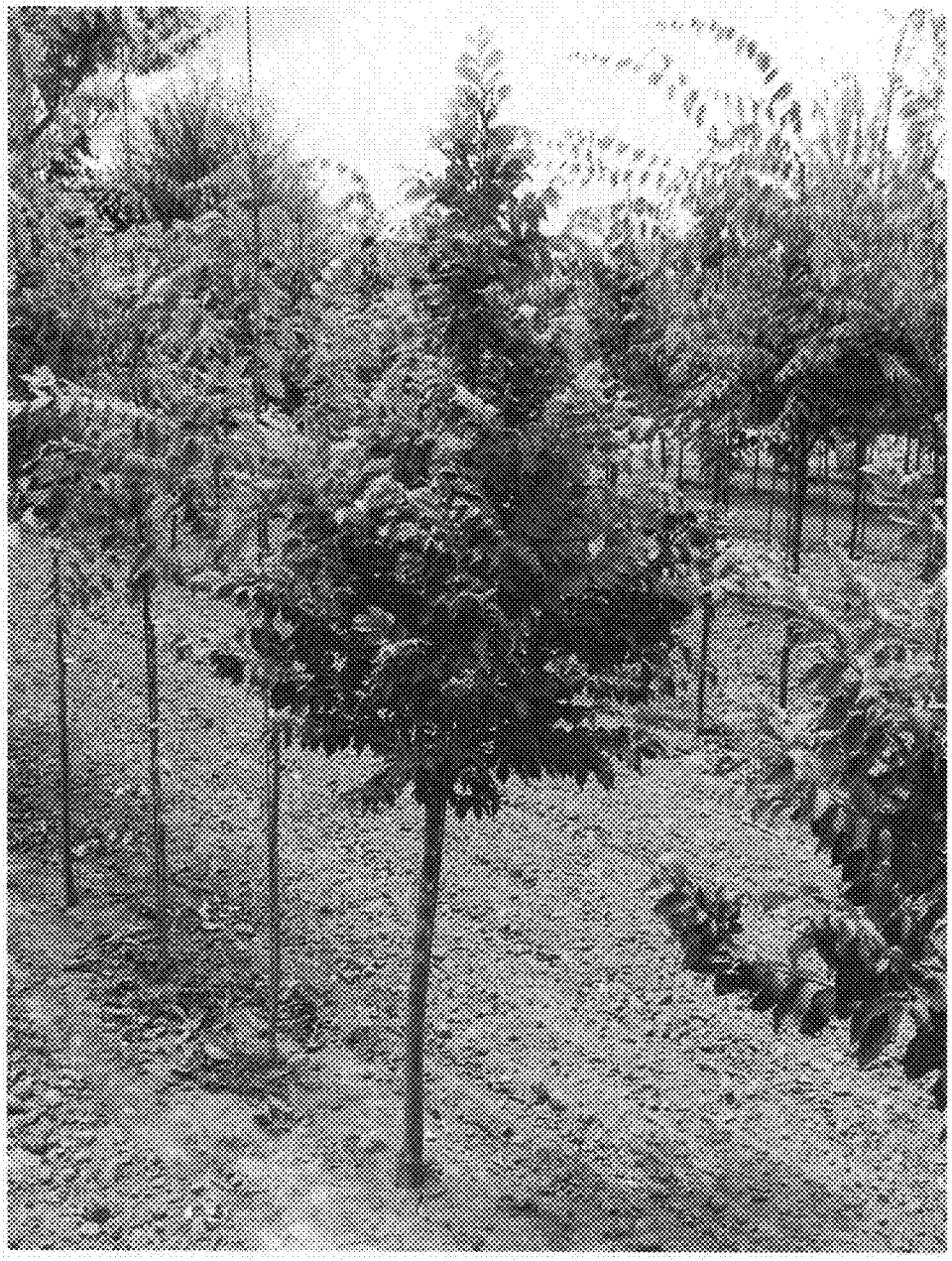
FIG. 3: Shows a 2 year old tree propagated by budding, illustrating its compact, dense form.
Figure 4:
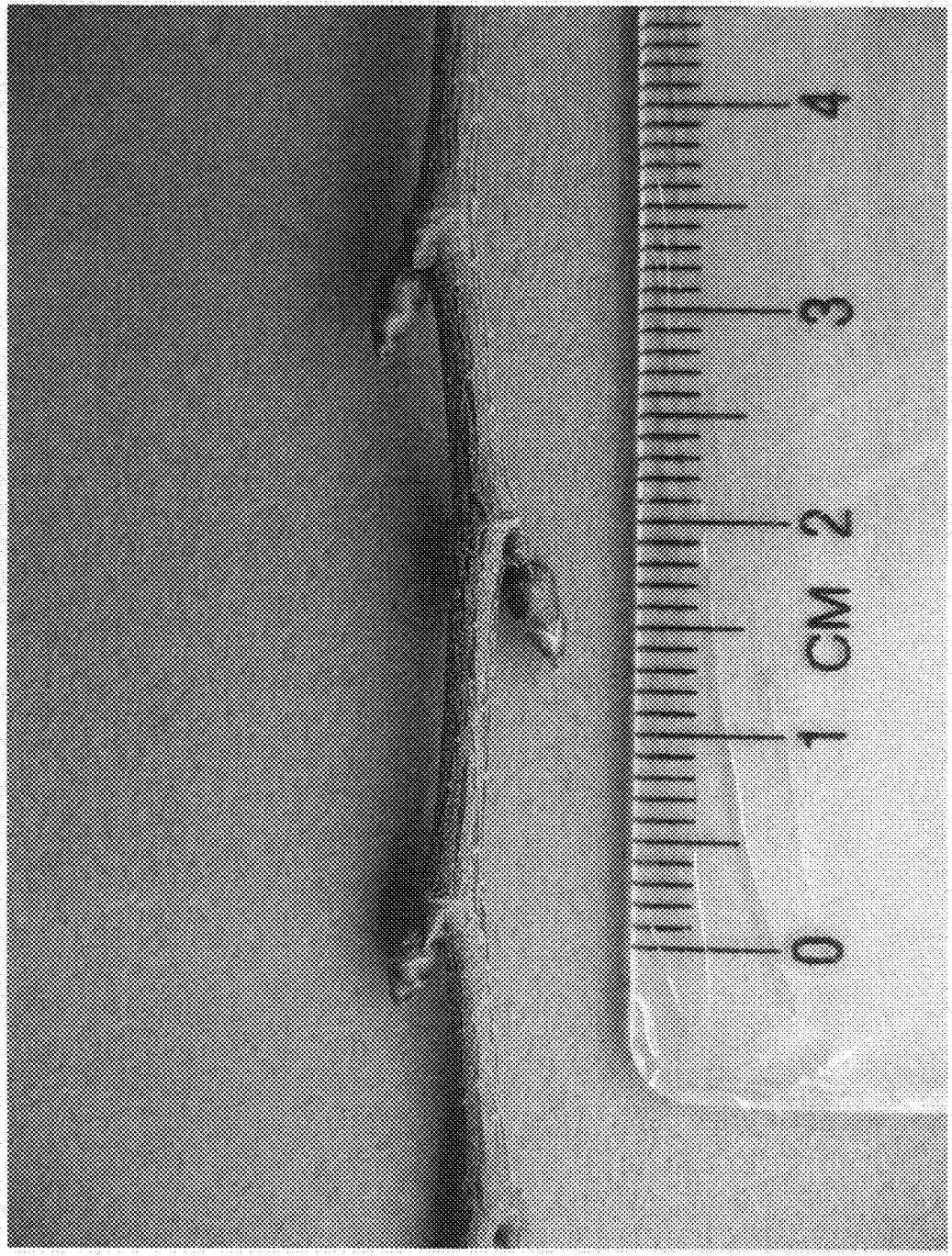
FIG. 4: Shows an exemplary dormant twig and buds and illustrates an example of the short internode length.
Figure 5:
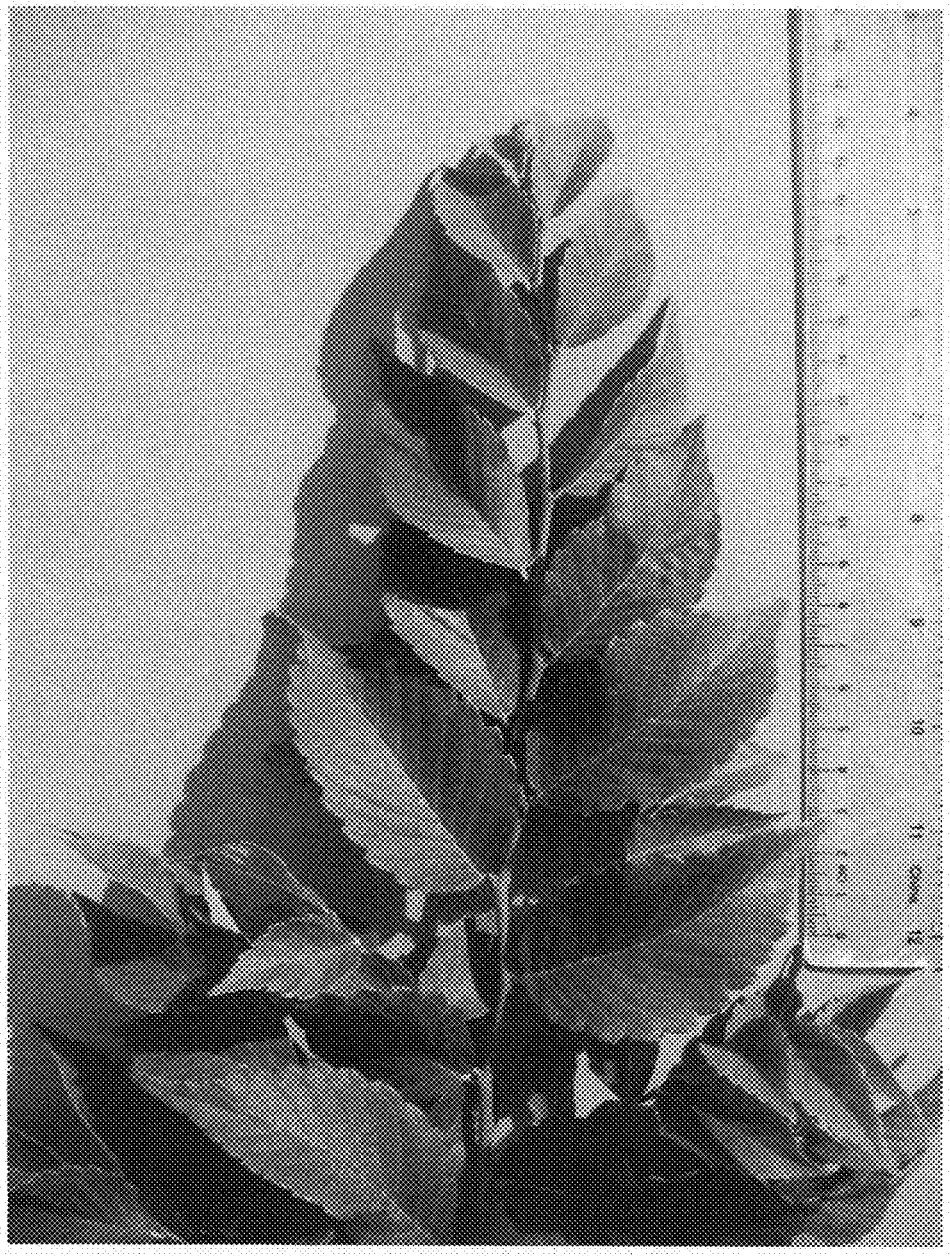
FIG. 5: Shows foliage in summer color.
Figure 6:
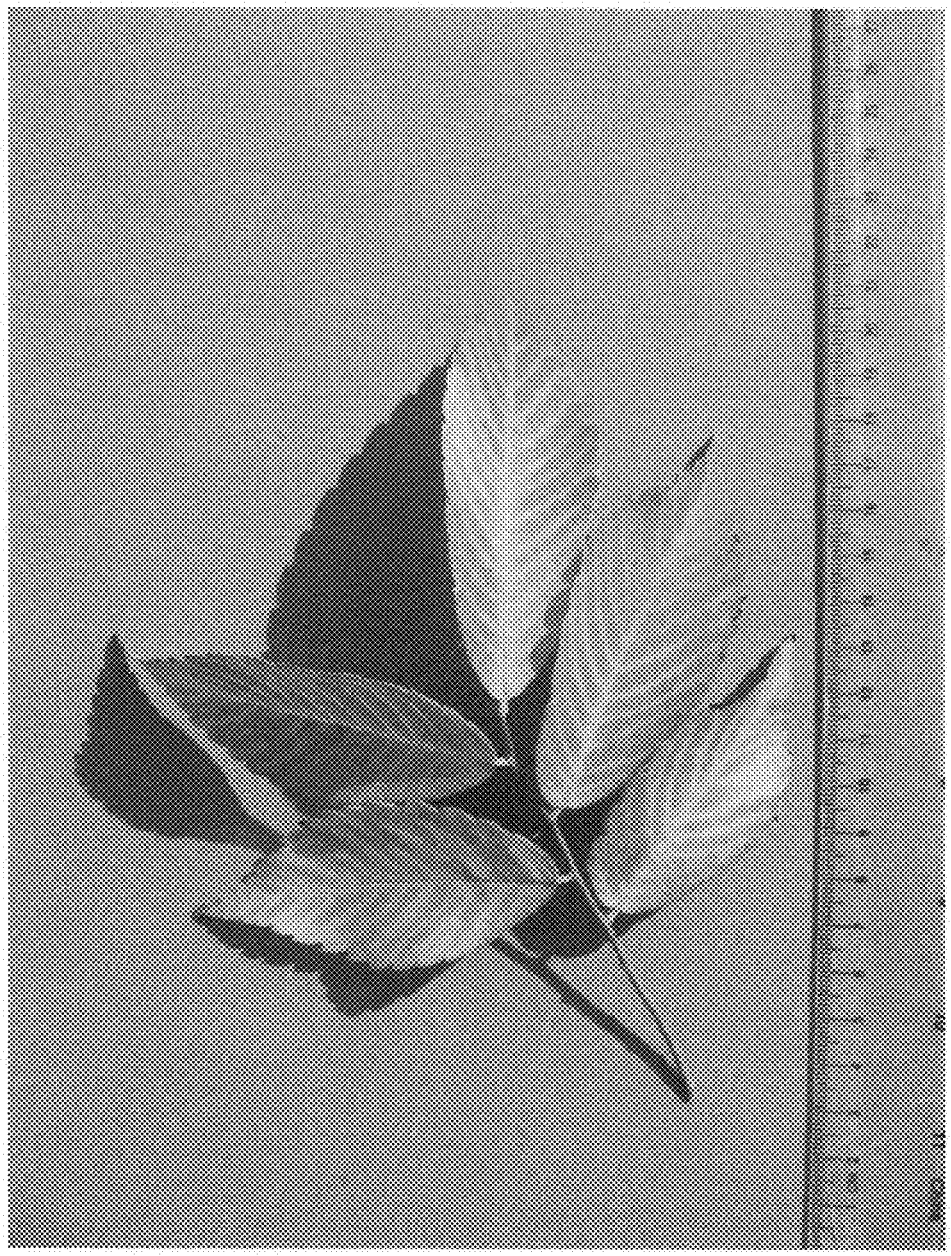
FIG. 6: Shows foliage in fall color.
Figure 7:
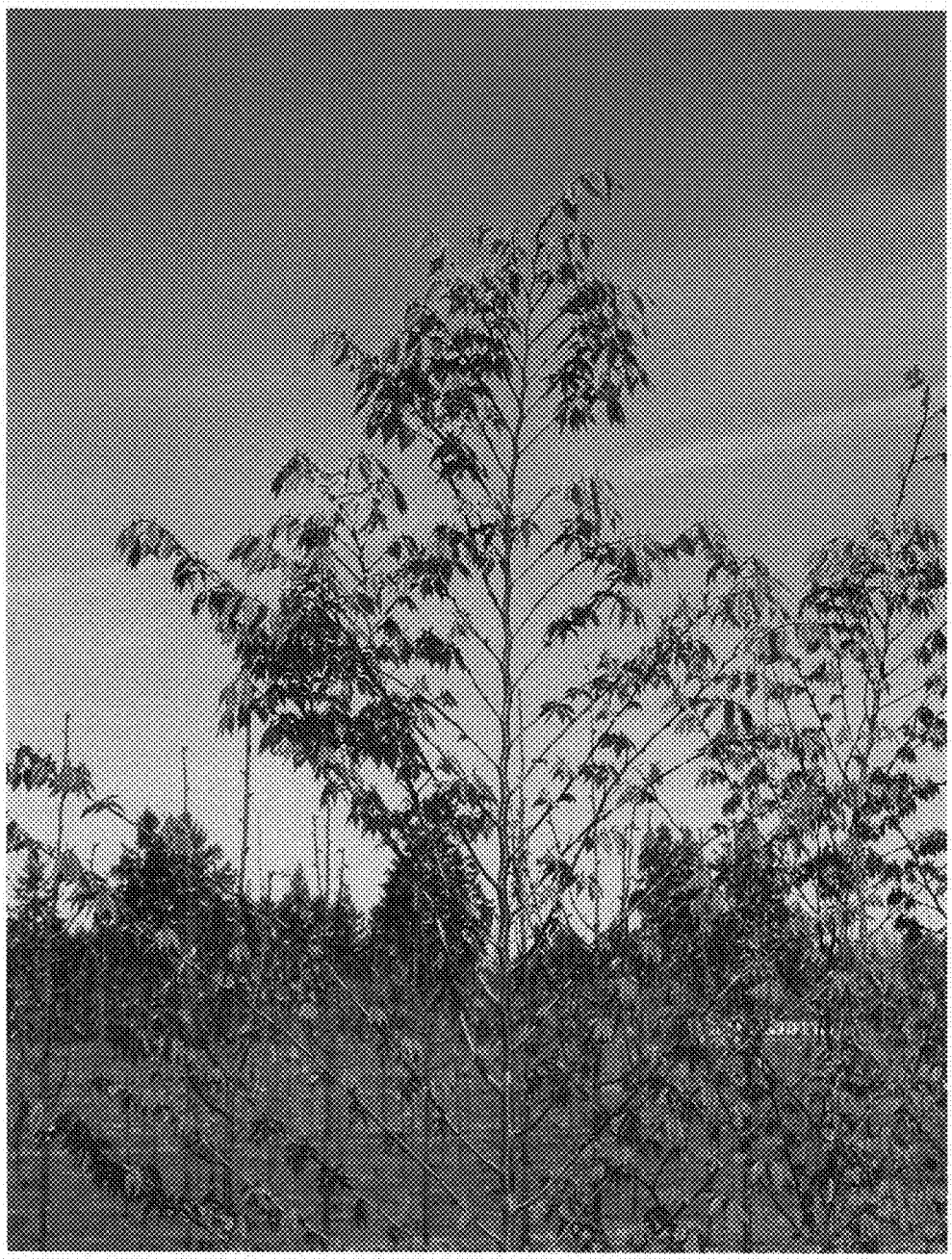
FIG. 7: Shows the branching of a top portion of the leader of a 3 year old tree as it leafs out in mid-April.

The following detailed description of the 'JFS-KW1' variety, with color terminology in accordance with The Royal Horticultural Society (R.H.S.) Colour Chart published by The Royal Horticultural Society in London, and is based on observations of the original 'JFS-KW1' tree growing in Boring, Oreg., and 1 year, 2 year, and 3 year old asexually propagated (by grafting) progeny thereof. The observed progeny were trees which were growing in Canby, Oreg.

Scientific name: *Zelkova serrata* 'JFS-KW1'.

Parentage:

*Seed parent.*—*Zelkova serrata.*

*Pollen parent.*—*Zelkova serrata.*

Tree:

*Overall shape.*—Densely pyramidal when young becoming upright oval by five years of age.

*Height.*—3.51 m at 10 years of age.

*Width.*—2.71 m at 10 years of age.

*Caliper.*—9.5 cm, measured 30 cm from ground, and 7.5 cm measured 1 m from ground, both at 10 years of age.

*Trunk.*—Straight, sturdy, with moderate taper.

*Trunk bark texture.*—Smooth.

*Trunk bark color.*—Immature bark color: Greyed-green RHS 195A. Mature bark color: Greyed-green RHS 197B to Grey-brown RHS 199B. Lenticels: Horizontal oblong in shape; 1 mm×3–5 mm; Grey-brown RHS 199B.

*Primary branches.*—Slender, heavily branched.

*Branch color.*—Greyed-orange RHS 177A in first year becoming Grey-brown RHS 199A in second and subsequent years.

*Branch lenticels.*—Oval, with longer dimension crosswise to the length of the branch; 1 mm×1–2 mm; Greyed-orange RHS 177A.

*Dormant buds.*—Very small, 1–4 mm long×1 mm wide, slender, acute with overlapping scales. Brown RHS 200A.

*Internodes.*—Very short, typically 12–29 mm, typically averaging 23 mm.

*Hardiness.*—No winter damage has been observed on 'JFS-KW1' growing in Boring, Oreg. or in Canby, Oreg., USDA Zone 8.

*Disease resistance.*—No disease has been observed on 'JFS-KW1'.

*Insect resistance.*—No insect damage has been observed on 'JFS-KW1'.

Leaves: Observations are of twenty vigorous growth leaves obtained at the same time.

*Arrangement.*—Alternate.

*Texture.*—Upper surface smooth, but directionally oriented pubescence gives the leaf a slightly roughened feel.

*Sheen.*—Dull to slightly satiny.

*Length.*—7–11 cm.

*Width.*—3.5–6.5 cm.

*Petioles.*—Short, 3 mm long×1 mm wide. Color: Yellow-green RHS 152C.

*Overall shape.*—Ovate to long ovate.

*Margin.*—Serrate. Each tooth has a short acuminate tip.

*Vein.*—Pinnately veined with a well defined central vein, pronounced on lower surface. Color: Yellow-green RHS 151A.

*Tip.*—Acuminate.

*Base.*—Rounded to sub-cordate.

*Stipules.*—None.

*Spring leaf color, first emerging leaves.*—Yellow-green RHS 152A with highlight tints of Greyed-orange RHS 176B on sun exposed portions of the upper surface.

*Summer leaf color.*—Upper leaf surface: Green RHS 139A. Lower leaf surface: Yellow-green RHS 147A to RHS 147B.

*Fall leaf color: Yellow RHS* 11A to Yellow-orange RHS 22A.

*Pubescence.*—Finely hirsute, with short stiff hairs on the upper leaf surface which are generally angled toward the leaf tip and very short, stiff, dense hairs growing at right angles to the leaf on the lower surface. Color: Translucent white, similar to White RHS 155A.

*Persistence.*—Tree is deciduous.

Flowers: None observed to date. The original tree and its progeny have not yet flowered.

Fruit: None observed to date. The original tree and its progeny have not yet set seed.

Comparison to Parent Species and Other Cultivars:

Japanese *Zelkova*, the parent species, is typically a spreading, vase shaped tree of medium to fast growth rate, with a somewhat loose and open growth habit and medium internode length.

Four Japanese *Zelkova* trees are understood to have been patented in the U.S.: U.S. Plant Pat. No. 2,337 'Village Green', U.S. Plant Pat. No. 5,080 'Green Vase', U.S. Plant Pat. No. 5,678 'Halka', and U.S. Plant Pat. No. 17,220 'ZSFKF'. All of these cultivars have been characterized as having faster than normal growth rate for the species. These prior cultivars also feature spreading, upright arching, or vase shaped growth habits.

My new tree, 'JFS-KW1', is a slow growing, compact, semi-dwarf tree with high density of branching as evidenced by the number of branches on the terminal growth shown in the table below. 'JFS-KW1' is much more dense, compact, and dwarf in nature than typical seedlings or any prior patented Japanese *Zelkova* or any other cultivar of Japanese *Zelkova* that I am aware of.

Comparison tables:

TABLE I 1 year old nursery trees, Canby, OR. Measured October 2007.

| | 'JFS-KW1' | 'Green Vase' | Seedling |
|---|---|---|---|
| Tree Height | 1.43 m | 2.50 m | 2.41 m |
| Internode Length | 23 mm | 46 mm | 44 mm |

TABLE II 3 year old nursery trees, Canby, OR. Measured October 2007.

| | 'JFS-KWl' | 'Green Vase' | Seedling |
|---|---|---|---|
| Tree Height | 2.83 m | 5.03 m | 4.88 m |
| Tree Width | 1.37 m | 2.53 m | 2.90 m |
| Number of branches on the top 30 cm of the central trunk (leader). | 13.5 | 0 | 0 |

I claim:

1. A new and distinct variety of Japanese *Zelkova* tree, substantially as herein shown and described.

* * * * *

UNITED STATES PATENT AND TRADEMARK OFFICE

CERTIFICATE OF CORRECTION

PATENT NO. : PP20,996 P2
APPLICATION NO. : 12/288997
DATED : May 18, 2010
INVENTOR(S) : Keith S. Warren It is certified that error appears in the above-identified patent and that said Letters Patent is hereby corrected as shown below:

In the Specification:

Column three, line 15, insert the following missing paragraph: --Growth rate when young: Very slow growing, attaining an average height of about 1.4 meters as a one year old nursery tree from budding and about 2.8 meters as a three year old tree from budding. The growth rate during the first three growing seasons resulted in trees of my new cultivar that had a height that is about 55% to 60% of the height of typical Zelkova serrata seedlings of the same age under comparable growing conditions.--

Signed and Sealed this
First Day of November, 2011

David J. Kappos

David J. Kappos
*Director of the United States Patent and Trademark Office*